United States Patent
Chung et al.

(10) Patent No.: US 9,874,574 B2
(45) Date of Patent: Jan. 23, 2018

(54) MARKER FOR DETECTING PROLIFERATION AND TREATMENT CAPACITIES OF ADIPOSE-DERIVED STEM CELL CULTURED IN MEDIUM CONTAINING EGF OR BFGF, AND USE THEREOF

(71) Applicants: KOREA RESEARCH INSTITUTE OF BIOSCIENCE AND BIOTECHNOLOGY, Daejeon (KR); ANTEROGEN CO. LTD., Seoul (KR)

(72) Inventors: Kyung Sook Chung, Daejeon (KR); Mi Hyung Kim, Seoul (KR)

(73) Assignees: ANTEROGEN CO. LTD., Seoul (KR); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 94 days.

(21) Appl. No.: 14/758,710

(22) PCT Filed: Jun. 11, 2014

(86) PCT No.: PCT/KR2014/005110
§ 371 (c)(1),
(2) Date: Jun. 30, 2015

(87) PCT Pub. No.: WO2014/200256
PCT Pub. Date: Dec. 18, 2014

(65) Prior Publication Data
US 2016/0178648 A1 Jun. 23, 2016

(30) Foreign Application Priority Data
Jun. 12, 2013 (KR) ........................ 10-2013-0067365

(51) Int. Cl.
*C12Q 1/68* (2006.01)
*G01N 33/74* (2006.01)

(52) U.S. Cl.
CPC ........... *G01N 33/74* (2013.01); *C12Q 1/6883* (2013.01); *C12Q 2600/106* (2013.01); *C12Q 2600/118* (2013.01); *G01N 2333/726* (2013.01); *G01N 2500/10* (2013.01)

(58) Field of Classification Search
None
See application file for complete search history.

(56) References Cited

FOREIGN PATENT DOCUMENTS

| KR | 10-2010-0118491 A | 11/2010 |
|----|-------------------|---------|
| KR | 10-2012-0126284 A | 11/2012 |
| WO | WO 2010/037134 A2 | 4/2010 |
| WO | WO 2011/072119 A2 | 6/2011 |
| WO | WO 2013/162286 A1 | 10/2013 |

OTHER PUBLICATIONS

Sugino et al (Oncogene, 2007. vol. 26, pp. 7401-7413).*
Bunnell et al (Methods, 2008. vol. 45, pp. 115-120).*
Yun et al (Cellular Physiology, 2010. vol. 226, p. 559-571).*
Hu, F., et al., Cellular Reporgramming, vol. 15, pp. 224-232, (2013).
Gronthos, S. et al. (2001). Surface protein characterization of human adipose tissue-derived stromal cells. *Journal of Cellular Physiology*, 189(1), 54-63.
International Search Report, dated Sep. 1, 2014 in connection with PCT International Application No. PCT/KR2014/005110, filed Jun. 11, 2014.
Written Opinion of the International Searching Authority, dated Sep. 1, 2014 in connection with PCT International Application No. PCT/KR2014/005110, filed Jun. 11, 2014.
Tapp, H., et al. exp. Biol. Med. Bol. 234, pp. 1-9, (2009).
Extended European Search Report dated Dec. 5, 2016 in connection with European Application No. 14810983.8.
Manferdini Cristina et al: "Adipose-derived mesenchymal stem cells exert antiinflammatory effects on chondrocytes and synoviocytes from osteoarthritis patients through prostaglandin E2.", Arthritis and Rheumatism May 2013, vol. 65, No. 5, May 2013 (May 2013), pp. 1271-1281, XP002764503, ISSN: 1529-0131.
Gimble Jeffrey M et al: "Adipose-derived stem cells for regenerative medicine.", Circulation Research May 11, 2007, vol. 100, No. 9, May 11, 20007 (May 11, 2007), pp. 1249-1260, Xp002764504, ISSN:1524-4571.
Byung-Chul Lee et al: "PGE2 maintains self-renewal of human adult stem cells via EP2-mediated autocrine signaling and its production is regulated by cell-to-cell contact", Scientific Reports, vol. 6, May 27, 2016 (May 27, 2016), p. 26298, XP055321874., DOI: 10.1038/srep26298.
Office Action issued Jun. 21, 2017 in connection with Chinese Patent Application No. 201480010288.9 including English language translation thereof (Exhibit 1).
Sales, K. J., Grant, V., Catalano, R. D., & Jabbour, H. N. (2010). Chorionic gonadotrophin regulates CXCR4 expression in human endometrium via E-series prostanoid receptor 2 signalling to PI3K-ERK1/2: implications for fetal-maternal crosstalk for embryo implantation. Molecular human reproduction, 17(1), 22-32. (Exhibit 2).

* cited by examiner

*Primary Examiner* — Celine X Qian
(74) *Attorney, Agent, or Firm* — John P. White; Cooper & Dunham LLP

(57) ABSTRACT

The present invention relates to: a composition for detecting a marker for detecting the proliferation capacity or treatment capacity of adipose-derived stem cells cultured in a medium containing epidermal growth factor (EGF) or basic fibroblast growth factor (bFGF); and a detection method.

6 Claims, 10 Drawing Sheets

SEQUENCE LISTING

```
<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: RPL13A forward primer

<400> SEQUENCE: 1
catcgtggct aaacaggtac tg                                          22

<210> SEQ ID NO 2
<211> LENGTH: 19
<212> TYPE: DNA
<213> ORGANISM: Artificial Sequence
<220> FEATURE:
<223> OTHER INFORMATION: RPL13A reverse primer

<400> SEQUENCE: 2
gcacgacctt gagggcagc                                              19

<210> SEQ ID NO 3
<211> LENGTH: 20
<212> TYPE: DNA
<213> ORGANISM: Artificial Sequence
<220> FEATURE:
<223> OTHER INFORMATION: AGPAT9 forward primer

<400> SEQUENCE: 3
aatcttgaca acggatggat                                             20
```

```
<210> SEQ ID NO 4
<211> LENGTH: 20
<212> TYPE: DNA
<213> ORGANISM: Artificial Sequence
<220> FEATURE:
<223> OTHER INFORMATION: AGPAT9 reverse primer

<400> SEQUENCE: 4
caaaccagac atgaggacaa                                                   20

<210> SEQ ID NO 5
<211> LENGTH: 20
<212> TYPE: DNA
<213> ORGANISM: Artificial Sequence
<220> FEATURE:
<223> OTHER INFORMATION: ANXA10 forward primer

<400> SEQUENCE: 5
cgagacaaac cagcctattt                                                   20

<210> SEQ ID NO 6
<211> LENGTH: 20
<212> TYPE: DNA
<213> ORGANISM: Artificial Sequence
<220> FEATURE:
<223> OTHER INFORMATION: ANXA10 reverse primer

<400> SEQUENCE: 6
tggtcagcag gtctatttca                                                   20

<210> SEQ ID NO 7
<211> LENGTH: 20
<212> TYPE: DNA
<213> ORGANISM: Artificial Sequence
<220> FEATURE:
<223> OTHER INFORMATION: IGF2BP3 forward primer

<400> SEQUENCE: 7
cacctgatga gaatgaccaa                                                   20

<210> SEQ ID NO 8
<211> LENGTH: 20
<212> TYPE: DNA
<213> ORGANISM: Artificial Sequence
<220> FEATURE:
<223> OTHER INFORMATION: IGF2BP3 reverse primer

<400> SEQUENCE: 8
actttgcaga gccttctgtt                                                   20

<210> SEQ ID NO 9
<211> LENGTH: 20
<212> TYPE: DNA
<213> ORGANISM: Artificial Sequence
<220> FEATURE:
<223> OTHER INFORMATION: PTGER2 forward primer

<400> SEQUENCE: 9
cacctcattc tcctggctat                                                   20

<210> SEQ ID NO 10
<211> LENGTH: 20
<212> TYPE: DNA
<213> ORGANISM: Artificial Sequence
<220> FEATURE:
<223> OTHER INFORMATION: PTGER2 reverse primer
```

-continued

```
<400> SEQUENCE: 10
gaggtcccat ttttcctttc                                              20

<210> SEQ ID NO 11
<211> LENGTH: 20
<212> TYPE: DNA
<213> ORGANISM: Artificial Sequence
<220> FEATURE:
<223> OTHER INFORMATION: ITGA11 forward primer

<400> SEQUENCE: 11
tgaggtccct aaaagcactc                                              20

<210> SEQ ID NO 12
<211> LENGTH: 20
<212> TYPE: DNA
<213> ORGANISM: Artificial Sequence
<220> FEATURE:
<223> OTHER INFORMATION: ITGA11 reverse primer

<400> SEQUENCE: 12
cagtcctctt gcttggagat                                              20

<210> SEQ ID NO 13
<211> LENGTH: 20
<212> TYPE: DNA
<213> ORGANISM: Artificial Sequence
<220> FEATURE:
<223> OTHER INFORMATION: PAWR forward primer

<400> SEQUENCE: 13
caggagccac ctagaacagt                                              20

<210> SEQ ID NO 14
<211> LENGTH: 20
<212> TYPE: DNA
<213> ORGANISM: Artificial Sequence
<220> FEATURE:
<223> OTHER INFORMATION: PAWR reverse primer

<400> SEQUENCE: 14
tacctgaaac atttgcatcc                                              20

<210> SEQ ID NO 15
<211> LENGTH: 20
<212> TYPE: DNA
<213> ORGANISM: Artificial Sequence
<220> FEATURE:
<223> OTHER INFORMATION: SFRP2 forward primer

<400> SEQUENCE: 15
aaaatcatcc tggagaccaa                                              20

<210> SEQ ID NO 16
<211> LENGTH: 20
<212> TYPE: DNA
<213> ORGANISM: Artificial Sequence
<220> FEATURE:
<223> OTHER INFORMATION: SFRP2 reverse primer

<400> SEQUENCE: 16
tgtcgttcat ctcctcacag                                              20
```

MARKER FOR DETECTING PROLIFERATION AND TREATMENT CAPACITIES OF ADIPOSE-DERIVED STEM CELL CULTURED IN MEDIUM CONTAINING EGF OR BFGF, AND USE THEREOF

CROSS-REFERENCE TO RELATED APPLICATIONS

This application is a §371 national stage of PCT International Application No. PCT/KR2014/005110, filed Jun. 11, 2014, claiming priority of Korean Patent Application No. 10-2013-0067365, filed Jun. 12, 2013, the contents of each of which are hereby incorporated by reference in their entirety.

REFERENCE TO A SEQUENCE LISTING

This application incorporates-by-reference nucleotide and/or amino acid sequences which are present in the file named "160216_87762_Substitute_Sequence_Listing_DH.txt," which is 3.5 kilobytes in size, and which was created Feb. 12, 2016 in the IBM-PC machine format, having an operating system compatibility with MS-Windows, which is contained in the text file filed Feb. 16, 2016 as part of this application.

TECHNICAL FIELD

The present invention relates to a composition for detecting a marker capable of detecting proliferation or therapeutic potentials of adipose-derived stem cells cultured in a medium containing epidermal growth factor (EGF) or basic fibroblast growth factor (bFGF), and a detection method thereof.

BACKGROUND ART

Because adipose tissues contain 1000 times more stems cells than that may be obtained from the equal amount of bone marrow, various research has been conducted to use adipose tissue-derived stem cells (ASC) as materials for implantation. Further, adipose-derived stem cells are multipotent like marrow-derived stem cells and thus can be differentiated into cartilages, bones, adipocytes, muscle cells, etc. Furthermore, adipose-derived stem cells share similarities with marrow-derived stem cells in expressing cell-surface markers, and have been reported not to induce immune responses to both in vivo and in vitro autotransplantation or xenotransplantation, but rather exhibit potentials in regulating immune responses, thereby gaining attention as an effective method for cell-based therapies.

However, if adipose-derived stem cells are cultured in vitro by a standard culturing method using a conventionally known basal medium, the cell culture requires a lot of time, thereby making it difficult to obtain a clinically effective number of cells. Therefore, the standard culturing method has a disadvantage of low effectiveness in actual clinical applications. In this regard, the present inventors aimed to develop a culturing method for effective clinical treatment methods, and confirmed that adipose-derived stem cells cultured in a growth medium containing epidermal growth factor (EGF) or basic fibroblast growth factor exhibit superior clinical effects compared to adipose-derived stem cells cultured by the standard culturing method (KR Patent Application Publication No, 10-2010-0118491). However, objective analysis on molecular biological, features related to the superior clinical effects of the adipose-derived stem cells cultured in a medium containing EGF or bFGF has not yet been provided.

Especially, for reproducible production of stem cell therapeutic agents having treatment effects above a certain level as an actual medicine, while demonstrating excellent proliferation and therapeutic potentials of stem cells cultured in a growth medium compared to stem cells cultured in a basal medium, it is needed to develop a method for quality control examination to which medicinal effects such as differentiation potential, proliferation potential, and potency of stem cells obtained by an improved culturing method using a growth medium may be applied. Especially, in order to develop a method of evaluating an increase in a yield of cell therapeutic agents and the quality of therapeutic agents, a biomarker capable of representing such is needed.

DISCLOSURE

Technical Problem

Adipose-derived stem cells exhibit superior proliferation potential which enables maintaining the features of stem cells even after long-term subcultures and exhibit high therapeutic effects as well as differentiation potentials when cultured in a growth medium, compared to when cultured in a basal medium. In this regard, the present inventors aimed to develop a marker which shows expression differences between adipose-derived stem cells cultured in a basal medium and adipose-derived stem cells cultured in a growth medium, and observed that gene expressions of 1-acylglycerol-3-phosphate O-acyltransferase 9 (AGPAT9), annexin A10 (ANXA10), insulin-like growth factor 2 binding protein 3 (IGF2BP3), and prostaglandin E receptor 2 (PTGER2) are increased, and gene expressions of integrin alpha 11 (ITGA11), PRKC apoptosis WT1 regulator protein (PAWR), and secreted frizzled-related protein 2 (SFRP2) are reduced in adipose-derived stem cells cultured in a growth medium. Therefore, the present inventors confirmed that the genes may be used for measuring therapeutic activity, etc., as well as proliferation, immunosuppressive potential, differentiation potential, etc., of adipose-derived stem cells cultured a growth medium, and completed the present invention.

Technical Solution

An objective of the present invention is to provide a composition detecting a marker capable of detecting therapeutic potential of adipose-derived stem cells cultured in a medium containing epidermal growth factor (EGF) or basic fibroblast growth factor (bFGF), comprising an agent for measuring the level of mRNA or a protein of at least one gene selected from the group consisting of 1-acylglycerol-3-phosphate O-acyltransferase 9 (AGPAT9), annexin A10 (ANXA10), insulin-like growth factor 2 binding protein 3 (IGF2BP3), prostaglandin receptor 2 (PTGER2), integrin, alpha 11 (ITGA11), PRKC, apoptosis, WT1, regulator (PAWR), and secreted frizzled-related protein 2 (SFRP2).

Another objective of the present invention is to provide a composition for detecting a marker capable of detecting proliferation potential of adipose-derived stem cells cultured in a medium containing EGF or bFGF, comprising an agent for measuring the level of mRNA or a protein of at least one gene selected from the group consisting of AGPAT9, ANXA10, IGF2BP3, PTGER2, ITGA11, PAWR, and SFRP2.

Another objective of the present invention is to provide a kit for detecting a marker capable of detecting therapeutic or proliferation potentials or adipose-derived stem cells cultured in a medium containing EGF or bFGF, comprising the composition for detecting the marker.

Another objective of the present invention is to provide a method for detecting therapeutic or proliferation potentials of adipose-derived stem cells comprising a step of measuring the level of mRNA or a protein of at least one gene selected from the group consisting of AGPAT9, ANXA10, IGF2BP3, PTGER2, ITGA11, PAWR, and SFRP2 of adipose-derived stem cells cultured in a medium containing EGF or bFGF.

Advantageous Effects

The present invention provides a marker capable of detecting adipose-derived stem cells cultured in a growth medium having enhanced clinical effects, thereby providing even more effective data for verifying effects of adipose-derived stem cells. Further, the present invention may be effectively used as a marker capable of detecting therapeutic activities represented by proliferation potential, differentiation potential, etc., of adipose-derived stem cells cultured by an improved culturing method.

DESCRIPTION OF DRAWINGS

FIG. 4 illustrates changes in the amount of gene expressions, which increased in a growth medium in FIG. 3, in adipose-derived stem cells collected from 17 donors, demonstrated by RT-PCR and real-time PCR, in which PPL13A is the control gene.

FIG. 5 illustrates changes in an amount of gene expression, which decreased in a growth medium in FIG. 3, in adipose-derived stem cells collected from 17 donors, demonstrated by RT-PCR and real-time PCR, in which RPL13A is the control gene.

BEST MODE

Figure 1:
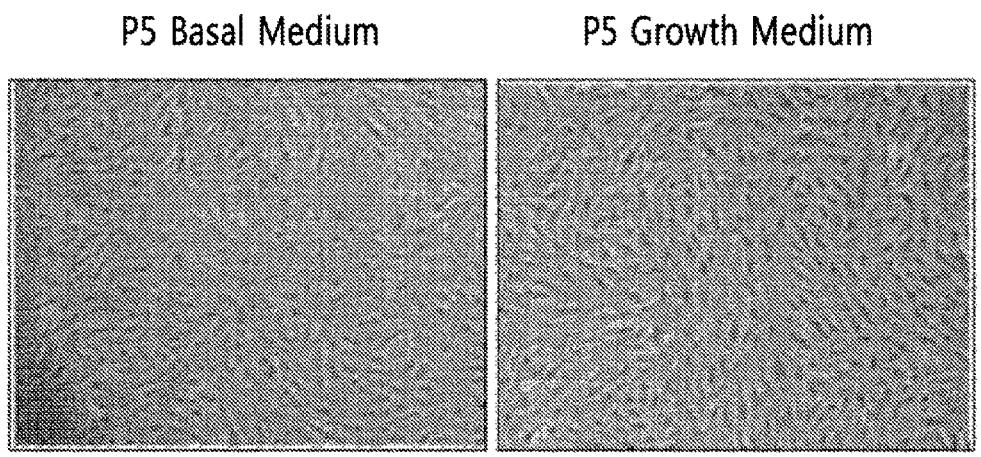
FIG. 1 illustrates cell morphologies of adipose-derived stem cells in a basal medium and a growth medium.

The present invention provides a composition for detecting a marker capable of detecting therapeutic potential of adipose-derived stem cells cultured in a medium containing EGF or bFGF, comprising an agent for measuring the level of mRNA or a protein of at least one gene selected from the group consisting of AGPAT9, ANXA10, IGF2BP3, PTGER2, ITGA11, PAWR, and SFRP2.

As used herein, the term "adipose-derived stem cell (ASC)" refers to stem cells isolated from adipose tissues, which are capable of differentiating into most mesenchymal cells such as adipocytes, osteoblasts, chondrocytes, myofibroblasts, etc., and which are also known as, preadipocytes, stromal cells, multipotent adipose-derived cells, adipose-derived adult stem cells, etc. The adipose-derived stem cells may be originated from mammals including pigs, cows, primates, humans, etc., which may be transplanted into humans, without being particularly limited thereto.

As used herein, the term "a marker capable of detecting therapeutic potential of adipose-derived stem cells cultured in a medium containing EGF or bFGF" refers to organic biomolecules which exhibit a significant difference in an expression level when adipose-derived stem cells cultured in a basal medium not containing EGF or bFGF, and adipose-derived stem cells cultured in a growth medium containing EGF or bFGF are compared. Further, adipose-derived stem cells cultured in a growth medium have superior therapeutic potential such as immunosuppression or differentiation potentials, etc., compared to adipose-derived stem cells cultured in a basal medium (KR Patent Application Publication No. 10-2010-0118491). Thus, the term refers to a marker capable of detecting therapeutic potential of adipose-derived stem cells by comparing an expression level to that of a basal medium, and specifically is at least one gene selected from the group consisting of AGPAT9, ANXA10, IGF2BP3, PTGER2, ITGA11, PAWR, and SFRP2, which shows increased expressions of AGPAT9, ANXA10, IGF2BP3, and PTGER2, and decreased expressions of ITGA11, PAWR, and SFRP2 in adipose-derived stem cells cultured in a growth medium compared to adipose-derived stem cells cultured in a basal medium.

Further, information of the genes used in the present invention may be obtained from a known database such as GenBank of the National Institutes of Health in the United States, etc., and examples thereof may include AGPAT9 (NM_032717.3, NP_001243351.1), ANXA10 (NM_007193.3, NP_009124.2), IGF2BP3 (NM_006547.2, NP_006538.2), PTGER2 (NM_000956.2, NP 000947.2), ITGA11 (NM_001004439.1, NP_001004439.1), PAWR (NM_002583.2, NP_002574.2), or SFRP2 (NM_003013.2, NP_003004.1), without being limited thereto.

When adipose-derived stem cells cultured in a basal medium and adipose-derived stem cells cultured in a growth medium are compared, the genes show differences in expression. In this regard, the genes may be used as a marker capable of detecting therapeutic potential of adipose-derived stem cells.

As used herein, the term "epidermal growth factor (EGF)" refers to a growth factor capable of stimulating cellular proliferation, growth, and differentiation by binding to its receptor EGFR. EGF acts to stimulate proliferation of various epithelial cells and is also capable of proliferating rat T-cells or human fibroblasts. According to the objectives of the present invention, EGF refers to proteins which serve the role of increasing therapeutic activities such as proliferation and differentiation potentials by being contained in a culture medium of adipose-derived stem cells.

As used herein, the term "basic fibroblast growth factor (bFGF)" refers to a growth factor is involved in biological processes such as angiogenesis or wound healing. According to the objectives of the present invention, bFGF, like EGF, refers to proteins which serve the role of increasing therapeutic ies as proliferation and differentiation potentials by being contained in a culture medium of adipose-derived stem cells.

As used herein, the term "basal medium" refers to a medium for culturing adipose-derived stem cells, especially a stromal vascular fraction containing such cells. The basal medium may be a DMEM medium, or a medium containing blood serum when culturing adipose-derived stem cells such as DMEM/F12, etc., wherein the serum may be fetal bovine serum (FBS) which are conventionally used for cell culture and may be contained at about 10%, i.e., 8% to 12%, but is not limited thereto as long as it is a culture medium for adipose-derived stem cells conventionally used in the art. In an embodiment of the present invention, a DMEM medium containing 10% FBS was used as a basal medium.

As used herein, the term "growth medium" refers to a medium for increasing proliferation or differentiation potentials of adipose-derived stem cells, which comprises basic fibroblast growth factor (bFGF) or epidermal growth factor (EGF) additionally to the basal medium. The growth medium may contain each of EGF and bFGF at a concentration of 0.1 ng/mL to 100 ng/mL. In the present invention, the term "growth medium" may be interchanged with a term "medium containing EGF or bFGF".

Information, etc., on the basal medium and growth medium is disclosed in KR Patent. Application Publication No. 10-2010-0118491, and the entire specification of KR Patent Application Publication No. 10-2010-0118491 may be included as a reference for the present invention, without being limited thereto.

As used herein, the term "therapeutic potential" refers to therapeutic activity of stem cells, and may be referred as "potency" when stem cells of the present invention are used as cell therapeutic agents, etc. Preferably, it refers to proliferation, differentiation, immunomodulatory potentials, or all of the above of adipose-derived stem cells, without being limited thereto.

As used herein, the term "differentiation potential" refers to potential of adipose-derived stem cells differentiating into adipocytes, osteoblasts, chondrocytes, myofibroblasts, as muscle cells, neurons, etc. In the present invention, adipose-derived stem cells with high differentiation potential refers to cells which are easily induced to differentiate into adipocytes, osteoblasts, chondrocytes, myofibroblasts, osteoblasts, muscle cells or neurons, without being limited thereto.

As used herein, the term "immunomodulatory potential" preferably refers to immunosuppression potential which refers to potential of adipose-derived stem cells cultured in a medium containing bFGF or EGF in suppressing activity of immune cells. Especially, mesenchymal stem cells are known to be involved in immunosuppression effects by suppressing antigen presenting cells (APCs). Thus, immune diseases may be treated using adipose-derived stem cells of the present invention as immunosuppressive agents.

As used herein, the term "adipose-derived stem cells with high therapeutic potential" refers to adipose-derived stem cells which have increased expressions of at least one gene selected from the group consisting of AGPAT9, ANXA10, IGF2BP3, and PTGER2, and reduced expressions of at least one selected from the group consisting of ITGA11, PAWR, and SFRP2, compared to adipose-derived stem cells cultured in a basal medium, and also refer to adipose-derived stem cells which have faster proliferation, better immunosuppression potential, differentiation efficiency, etc., thereby exhibiting better activity (potency) as a therapeutic agent, compared to adipose-derived stem cells cultured in a basal medium.

Expression levels of the genes may be examined by measuring mRNA or protein amounts (levels).

As used herein, the term "mRNA level measurement" refers to a process of examining existence and expression levels of mRNA of marker genes which represent therapeutic potential of adipose-derived stem cells in a biological sample in order to examine differentiation potential of adipose-derived, stem cells. The corresponding analysis methods may include RT-PCR, competitive RT-PCR, real-time RT-PCR, RNase protection assay (RPA), Northern blotting, DNA chip, etc., without being limited thereto. In one embodiment of the present invention, the mRNA levels of the genes were examined using RT-PCR and Real-time PCR (Example 3).

An agent for measuring mRNA levels of the gene is preferably a primer pair or a probe, and nucleotide sequences of AGPAT9, ANXA10, IGF2BP3, PTGER2, ITGA11, PAWR, and SFRP2 genes are represented by NM_032717.3, NM_007193.3, NM_006547.2, NM_000956.2, NM_001004439.1, NM_002583.2, and NM_003013.2, respectively. Thus, based on the sequences, one of ordinary skill in the art may design primers or probes which can specifically amplify particular regions of the genes.

As used herein, the term "primer" refers to a short nucleotide sequence having a free 3'-terminal hydroxyl group, which is capable of forming a base pair with a complementary template and functions as a starting point for template strand replication. In the present invention, it is preferred that a primer for AGPAT9 is a primer pair represented by SEQ ID NOS: 3 and 4, a primer for ANXA10 is a primer pair represented by SEQ ID NOS: 5 and 6, a primer for IGF2BP3 is a primer pair represented by SEQ ID NOS: 7 and 8, a primer for PTGER2 is a primer pair represented by SEQ ID NOS: 9 and 10, a primer for ITGA11 is a primer pair represented by SEQ ID NOS: 11 and 12, a primer for PAWR is a primer pair represented by SEQ ID NOS: 13 and 14, or a primer for SFRP2 is a primer pair represented by SEQ ID NOS: 15 and 16, without being limited thereto.

As used herein, the term "probes" refers to nucleic acid fragments of RNA, DNA, etc., consisting of several to hundreds of bases, which are capable of specifically binding to mRNA and are labeled which allows examining the existence of mRNA. Probes may be constructed in the form of oligonucleotide probes, single-stranded DNA probes, double-stranded DNA probes, RNA probes, etc. In the present invention, via hybridization using AGPAT9, ANXA10, IGF2BP3, PTGER2, ITGA11, PAWR, or SFRP2 polynucleotides and a complementary probe thereof, differentiation potential of adipose-derived stem cells was determined by whether a polynucleotide and a complementary probe hybridized. One of ordinary skill in the art may appropriately choose probes and hybridization conditions based on what is known in the art.

A primer of the present invention may initiate DNA synthesis in the presence of reagents and 4 different nucleoside triphosphates for polymerization (i.e., DNA polymerase or reverse transcriptase) in an appropriate buffer solution at appropriate temperature. A primer of the present invention is sense and antisense nucleic acids specific to each marker gene, having 7 to 50 nucleotide sequences. A primer may incorporate additional features which do not change the basic function of a primer as the starting point of DNA synthesis. A primer or probe of the present invention may be chemically synthesized by a phosphoramidite solid substrate method, or other widely known methods. The nucleotide sequence may also be modified by numerous methods known in the art. Non-limiting examples of such modification include methylation, capping, substitution of at least one native nucleotide to analogs, and modification between nucleotides as modification into uncharged connecting substances (e.g., methyl phosphonate, phosphotriester, phoshoroamidate, carbamate, etc.) or charged connecting substances (e.g., phosphorothioate, phosphorodithioate, etc.). A nucleic acid may contain at least one additional covalently bonded residues such as proteins (e.g., nucleases, toxins, antibodies, signal peptides, poly-L-lysine, etc.), inserting materials (e.g., acridine, psoralen, etc.), chelating agents (e.g., metals, radioactive metals, irons, oxidative metals, etc.), and alkylating agents. A nucleotide sequence of the present invention may also be modified using labels capable of directly or indirectly providing detectable signals. Examples of labels may include radioisotopes, fluorescent molecules, biotins, etc.

As used herein, the term. "protein level measurement" refers to a process of examining the existence and expression levels of proteins of marker genes which represent therapeutic potential of adipose-derived stem cells in a biological sample, in order to examine differentiation potential of adipose-derived stem cells. Preferably, the amount of proteins may be measured by using an antibody which specifically binds to a protein of the genes.

As used herein, the term "antibody" refers to a specific protein molecule which is distinguished by its antigenic localities. According to the objective of the present invention, an antibody specifically binds to a marker protein, particularly to a protein encoded by AGPAT9, ANXA10, IGF2BP3, PTGER2, ITGA11, PAWR, or SFRP2 which are the marker genes of the present invention, and includes all of polyclonal antibodies, monoclonal antibodies, and recombinant antibodies. Since marker proteins of the present invention are already investigated, antibodies using such may be easily produced by methods widely known in the art. Polyclonal antibodies may be produced by widely known methods in the art, which include injecting the marker protein antigens into animals followed by blood sampling and obtaining the blood serum which contains antibodies. The polyclonal antibodies may be produced from arbitrary animal hosts such as goats, rabbits, sheep, monkeys, horses, pigs, cows, dogs, etc. Monoclonal antibodies may be produced by widely known methods in the art such as a hybridoma method (Kohler and Milstein (1976) European Journal of Immunology 6:511-519), or a phage antibody library method (Clackson et al, Nature, 352:624-628, 1991; Marks et al, J. Mol. Biol., 222:58, 1-597, 1991), etc. Antibodies produced by such methods may be separated and purified by methods such as gel electrophoresis, dialysis, salt precipitation, ion exchange chromatography, or affinity chromatography. Further, antibodies of the present invention include not only a complete form in which two light chains of a full length and two heavy chains of a full length, but also a functional fragment of an antibody molecule. A Functional fragment of an antibody molecule refers to a fragment which at least has a capacity of binding to an antigen, and may include Fab, F(ab'), F(ab')$_2$, Fv, etc. Measuring methods at the protein level include Western blot, enzyme linked immunosorbent assay (ELISA), radioimmunoassay (RIA), radioimmunodiffusion, Ouchterlony immunodiffusion, rocket immunoelectrophoresis, tissue immunostaining, immunoprecipitation assay, complement fixation assay, fluorescence activated cell sorter (FACS), protein chip, etc., without being limited thereto. In an embodiment of the present invention, the protein levels were measured via Western blotting (Example 4).

Figure 5A:
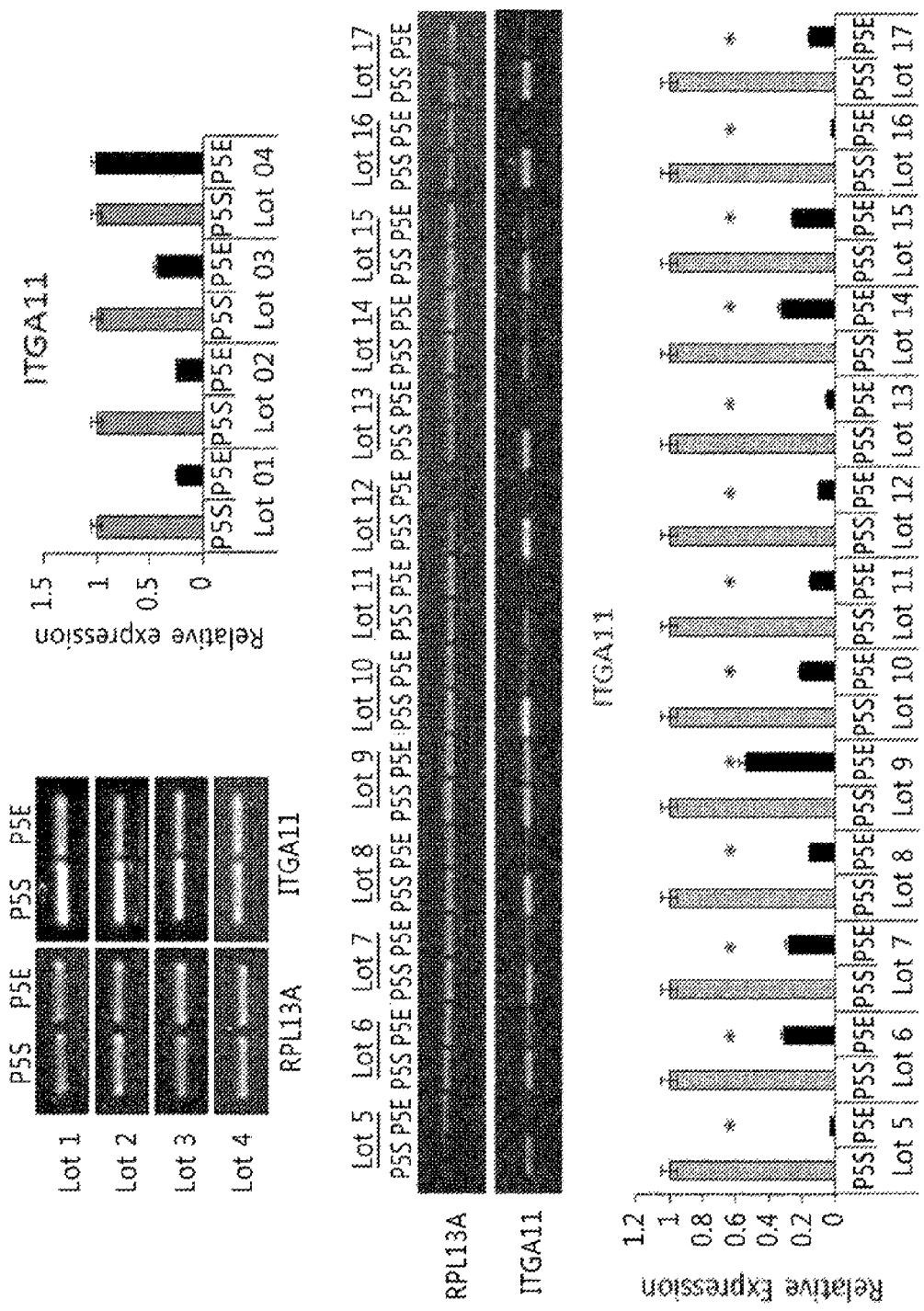
FIGS. 5A, 5B, and 5C respectively illustrate results of ITGA11, PAWR, and SFRP2, which decrease in a growth medium.
Figure 5B:
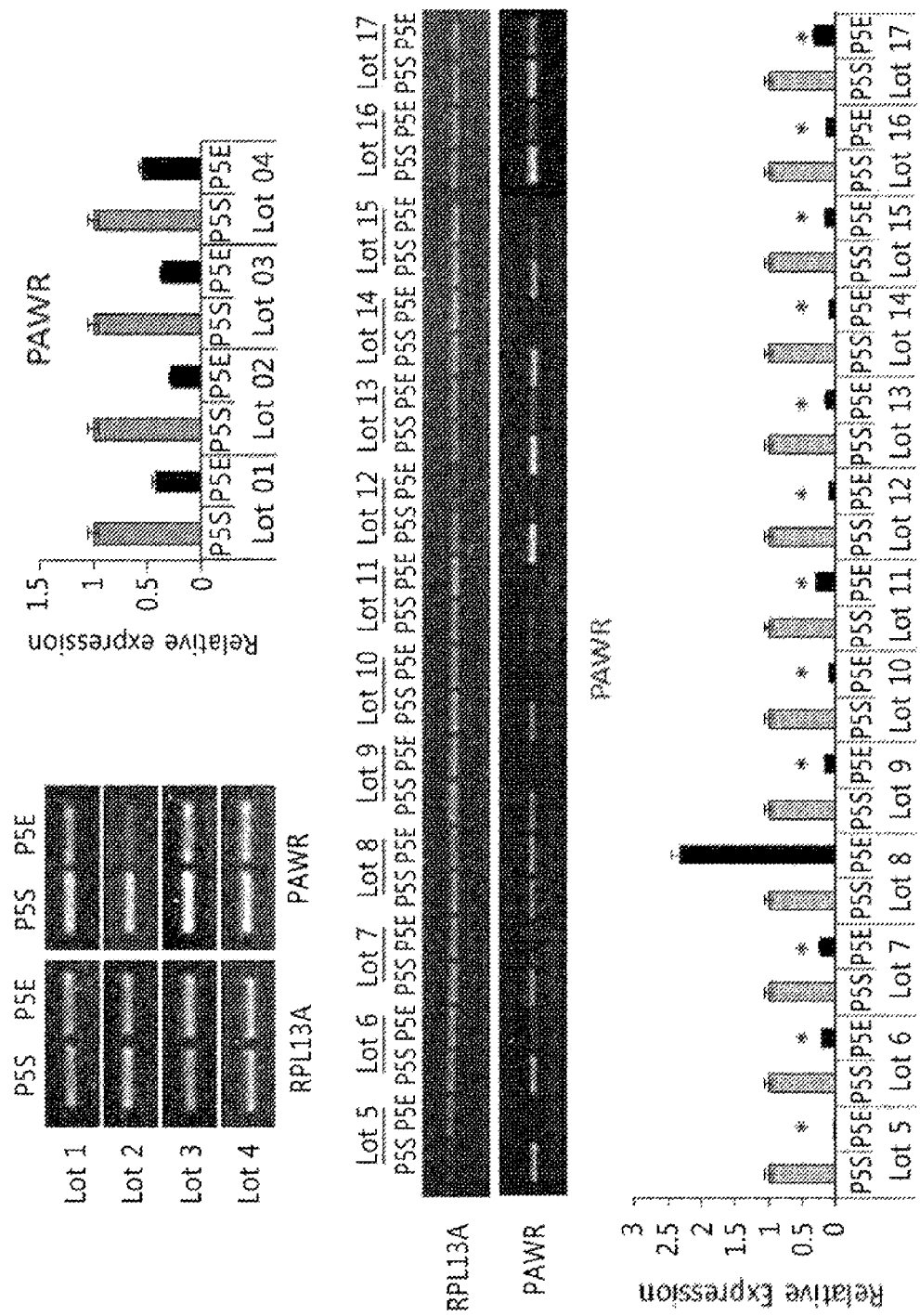
Figure 5C:
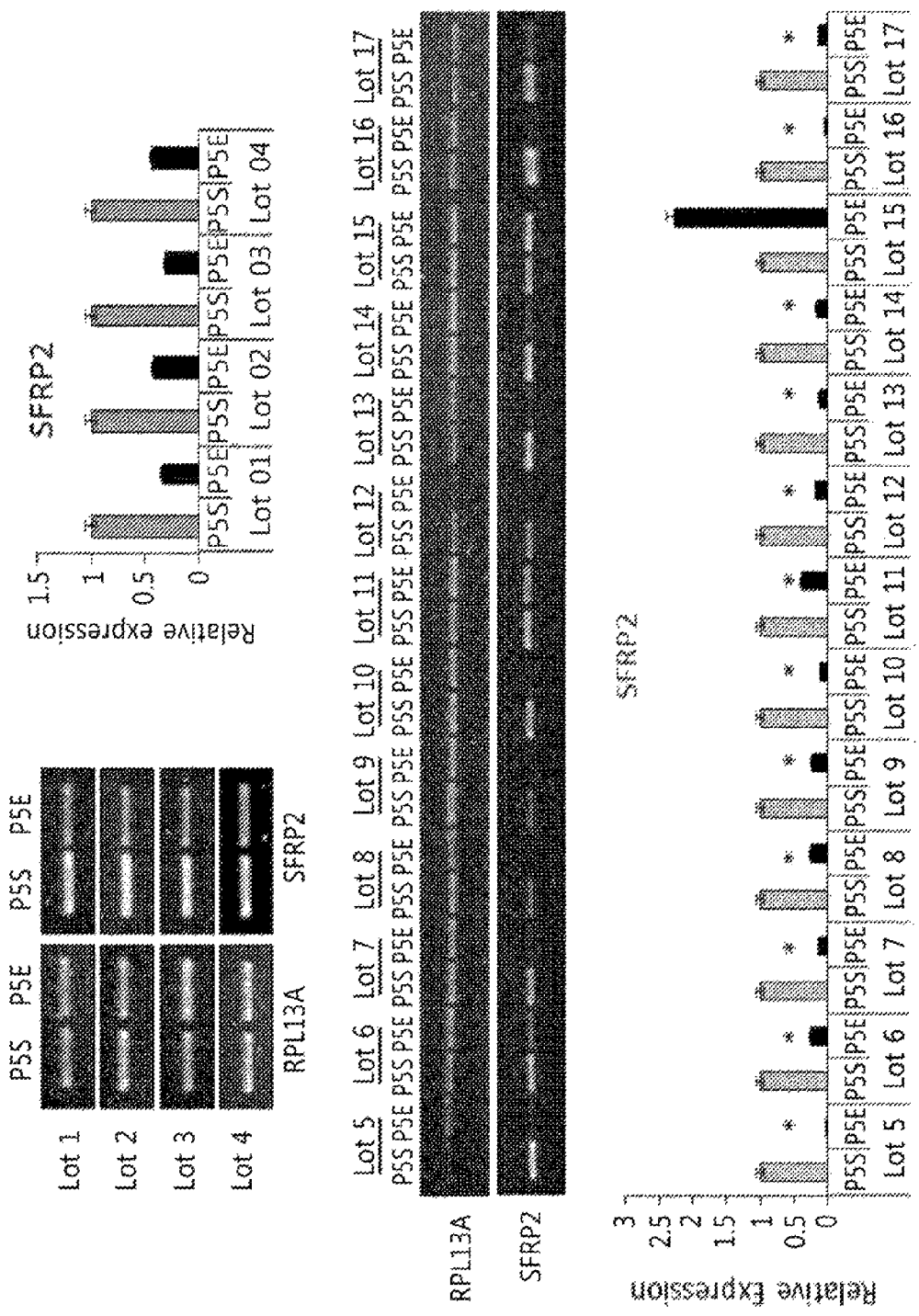
Figure 6:
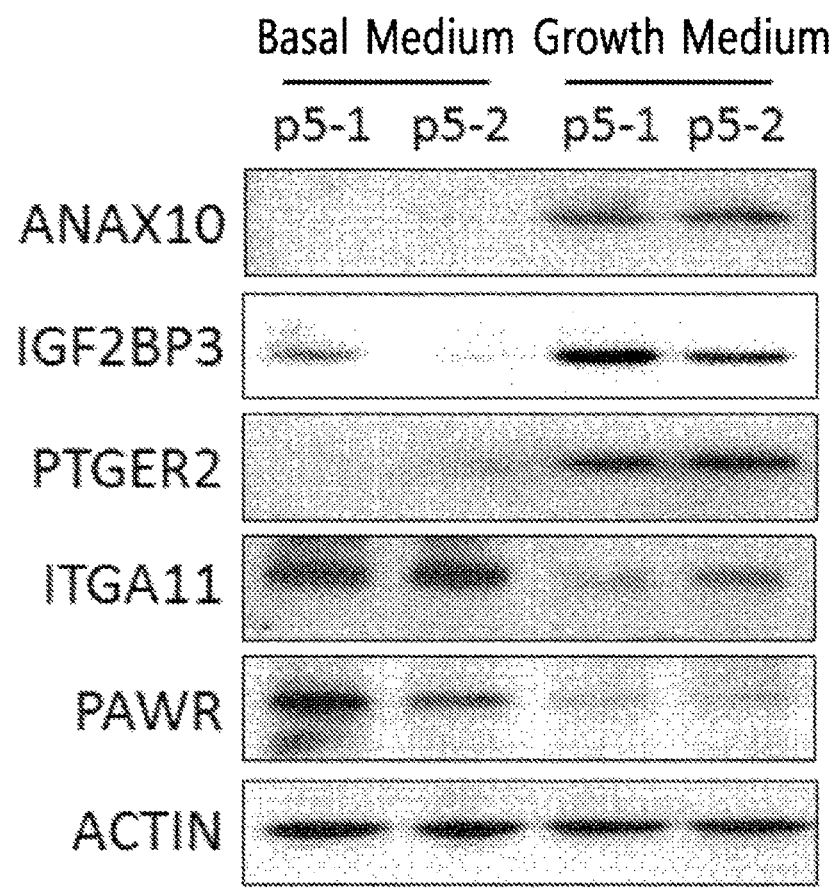
FIG. 6 illustrates protein changes of the genes in a basal medium and a growth medium.

In an embodiment of the present invention, based on that therapeutic activity such as proliferation potential, immunosuppression, differentiation potential, etc., is superior in adipose-derived stem cells cultured in a medium containing EGF or bFGF compared to adipose-derived stem cells cultured in a basal medium without the growth factors (KR Patent Application Publication No. 10-2010-0118491), genes which show significant expression differences between adipose-derived stem cells cultured in a medium containing EGF or bFGF and adipose-derived stem cells cultured in a basal medium were examined, and results confirmed increased expressions of AGPAT9, ANXA10, IGF2BP3, and PTGER2, and reduced expressions of ITGA11, PAWR, and SFRP2 in adipose-derived stem cells cultured in a medium containing EGF or bFGF (FIGS. 4 and 5). Thus, it was confirmed that highly expressed AGPAT9, ANXA10, IGF2BP3, and PTGER2 proteins and lowly expressed ITGA11, PAWR, or SFRP2 proteins may be used as markers for therapeutic activity of adipose-derived stem cells (FIG. 6).

In another aspect, the present invention provides a composition for detecting a marker capable of detecting proliferation potential of adipose-derived stem cells cultured in a medium containing EGF or bFGF, comprising an agent for measuring the level of mRNA or a protein of at least one gene selected from the group consisting of AGPAT9, ANXA10, IGF2BP3, PTGER2, ITGA11, PAWR, and SFRP2.

The adipose-derived stem cells, EGF, bFGF, mRNA or protein level measurement, and genes are as described above.

As used herein, the term "proliferation potential" refers to potential of increasing the number of cells involved in DNA synthesis or cell division stimulated by self-regulation or external stimuli such as hormones, and also includes the cases in which cells have potential to proliferate although not proliferating at the moment. Because stem cells have in vitro self renewal potential, they possess proliferation potential, but the proliferation potential decreases as culturing repeats for generations, having limitations in obtaining pure stem cells in a large quantity. Thus, in order to effectively use stem cells as therapeutic agents, a culturing method which enables obtaining stem cells in a large quantity in a short period of time is needed.

In the present invention, it was confirmed that, adipose-derived stem cells cultured in a medium containing EGF or bFGF exhibit superior proliferation potential, compared to adipose-derived stem cells cultured in a basal medium, and genes which show expression differences between adipose-derived stem cells which show difference in the proliferation potential cultured in a basal medium or a growth medium were examined. In particular, expressions of at least one gene selected from the group consisting of AGPAT9, ANXA10, IGF2BP3, and PTGER2 were increased, and expressions of at least one gene selected from the group consisting of ITGA11, PAWR, and SFRP2 was reduced in adipose-derived to cells cultured in a growth medium compared to adipose-derived stem cells cultured in a basal medium. Adipose-derived stem cells with such gene expressions exhibit superior proliferation compared adipose-derived stem cells cultured in a basal medium, especially compared to adipose-derived stem cells with reduced AGPAT9, ANXA10, IGT2BP3, or PTGER2 gene expressions or increased ITGA11, PAWR, or SFRP2 gene expressions, thereby increasing the yield of cells and showing features of high clinical therapeutic effects such as cell proliferation, immunosuppression, and differentiation potential.

Figure 2:
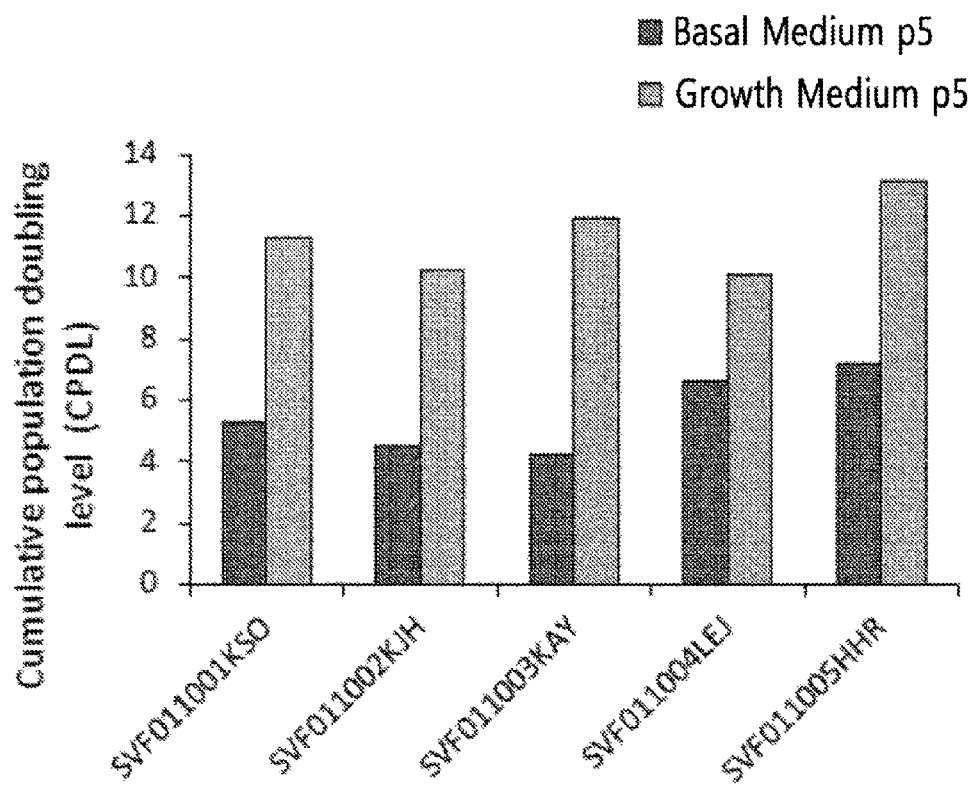
FIG. 2 illustrates cell growth differences of adipose-derived stem cells in a basal medium and a growth medium.

In one embodiment of the present invention, when the same amount of adipose-derived stem cells were cultured in a basal medium and a growth medium for five successive generations, cell proliferation was observed to be increased by twice or more on average in the growth medium (Example 1 and FIG. 2).

In another aspect, the present invention provides a kit for detecting a marker capable of detecting differentiation potential of adipose-derived stem cells cultured in a medium containing EGF or bFGF, comprising a composition for detecting a marker capable of detecting differentiation potential of the adipose-derived stem cells cultured in a medium containing EGF or bFGF.

A composition for detecting a marker capable of detecting differentiation potential of the adipose-derived stem cells cultured in a medium containing EGF or bFGF is the same as described above.

A kit for detecting a marker of the present invention comprises marker genes of which expression is increased or decreased depending on a growth medium containing EGF or BFGF for culturing, primers capable of specifically identifying proteins thereof, or antibodies, as well as tools and reagents which are generally used for immunological analysis in the art. The tools and reagents include appropriate carriers, markers capable of producing detectable signals, solvents, detergents, buffers, stabilizers, etc., without being limited thereto. When the markers are enzymes, substrates which allow measuring activity of enzymes and reaction stop agents may be included. Appropriate carriers may be soluble carriers such as physiologically acceptable buffers known in the art, such as PBS, insoluble carriers such as polystyrene, polyethylene, polypropylene, polyester, polyacrylonitrile, fluorine resin, crosslinked dextran, polysaccharide, polymers in which latex plated with metal similar to magnetic particles, other paper, glass, metals, agarose, and a combination thereof, without being limited thereto.

A kit for detecting a marker of the present invention may be preferably a RT-PCR kit, DNA kit, or protein chip kit. When antibodies to proteins encoded by the genes are provided in the protein chip, an antigen-antibody complex formation in relation to at least two antibodies may be observed, and thus the protein chip kit is more advantageous in detecting differentiation potential of adipose-derived stem cells.

The RT-PCR kit may include primer pairs which are each specific to the marker genes and also may include test, tubes or other appropriate containers, reaction buffer solutions (various pH and magnesium concentration), deoxynucleotides (dNTPs), enzymes such as Taq-polymerase and reverse transcriptase, DNAse, DNAse inhibitor, DEPC-water, sterilized water, etc.

The DNA chip kit may include a substrate to which a gene, cDNA or oligonucleotide corresponding to a fragment thereof is attached, reagents, formulation, enzymes, etc., for producing florescent-labeling probes. The substrate may include the control gene, or cDNA or oligonucleotide which corresponds to a fragment thereof.

The protein chip kit may be a kit in which at least one antibody to a marker is organized in predetermined locations on a substrate and is fixed at a high concentration. Protein chip may be used to examine the existence and expression level of proteins by isolating proteins from a sample, hybridizing isolated proteins with protein chips to form antigen-antibody complexes, and analyzing the results.

Figure 3:
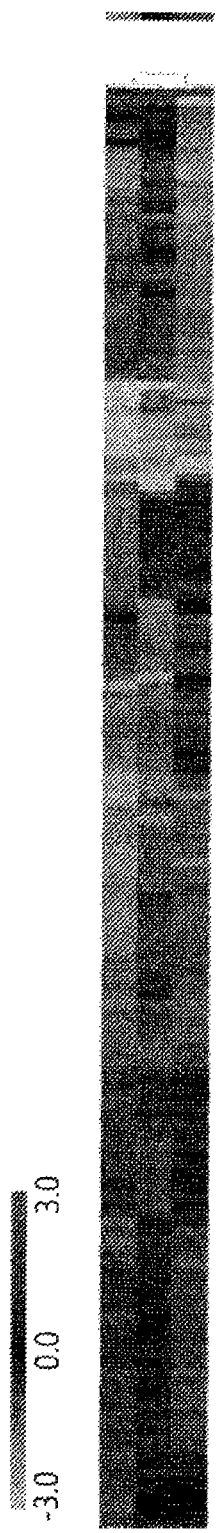
FIG. 3 illustrates of microarray results of cells cultured in 3 sets of basal media and adipose-derived stem cells cultured in growth media using Illumina 24K chip.
Figure 4A:
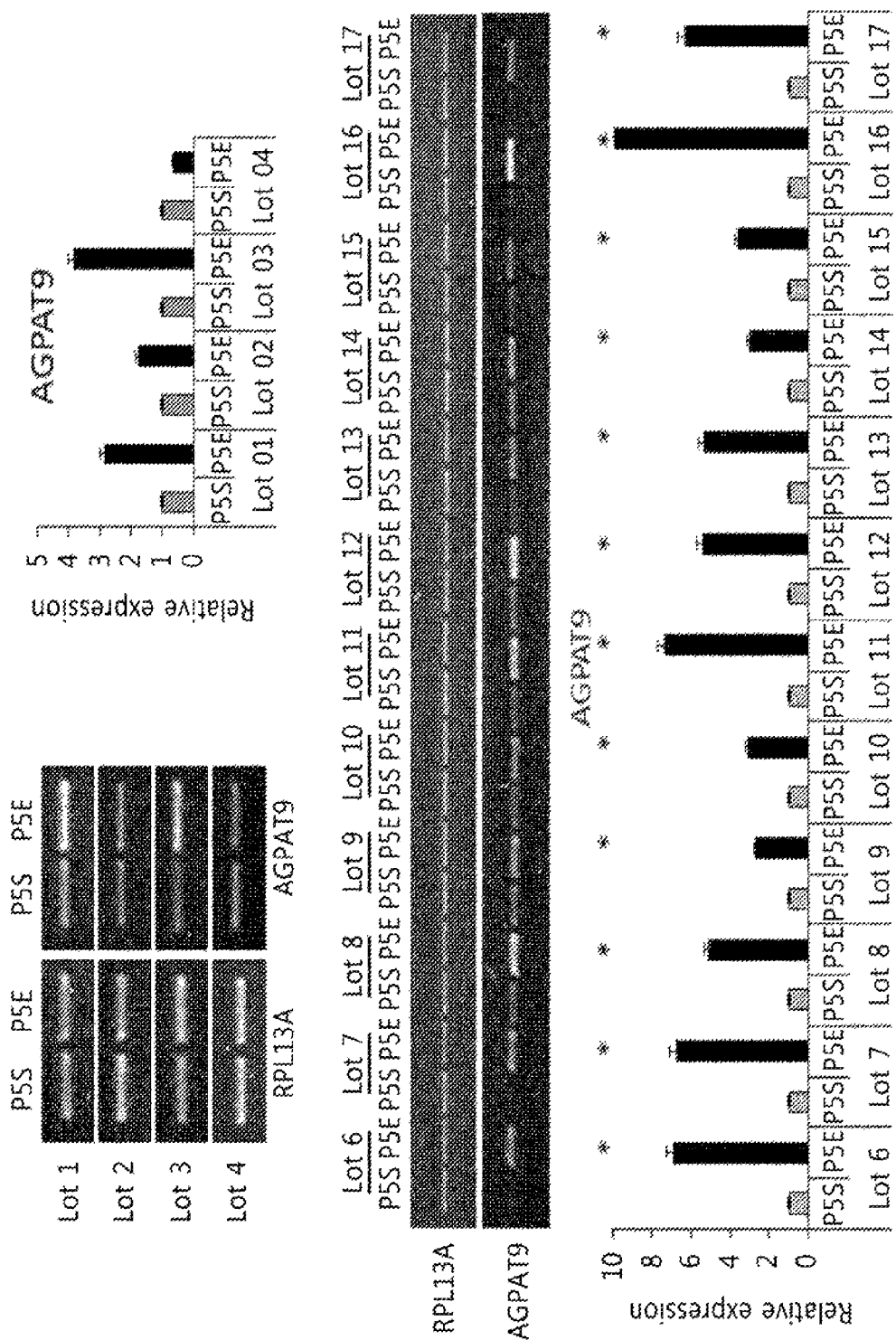
FIGS. 4A, 4B, 4C, and 4D respectively illustrate results of APPAT9, ANXA10, IGF2BP3, and PTGER2, which increase in a growth medium.
Figure 4B:
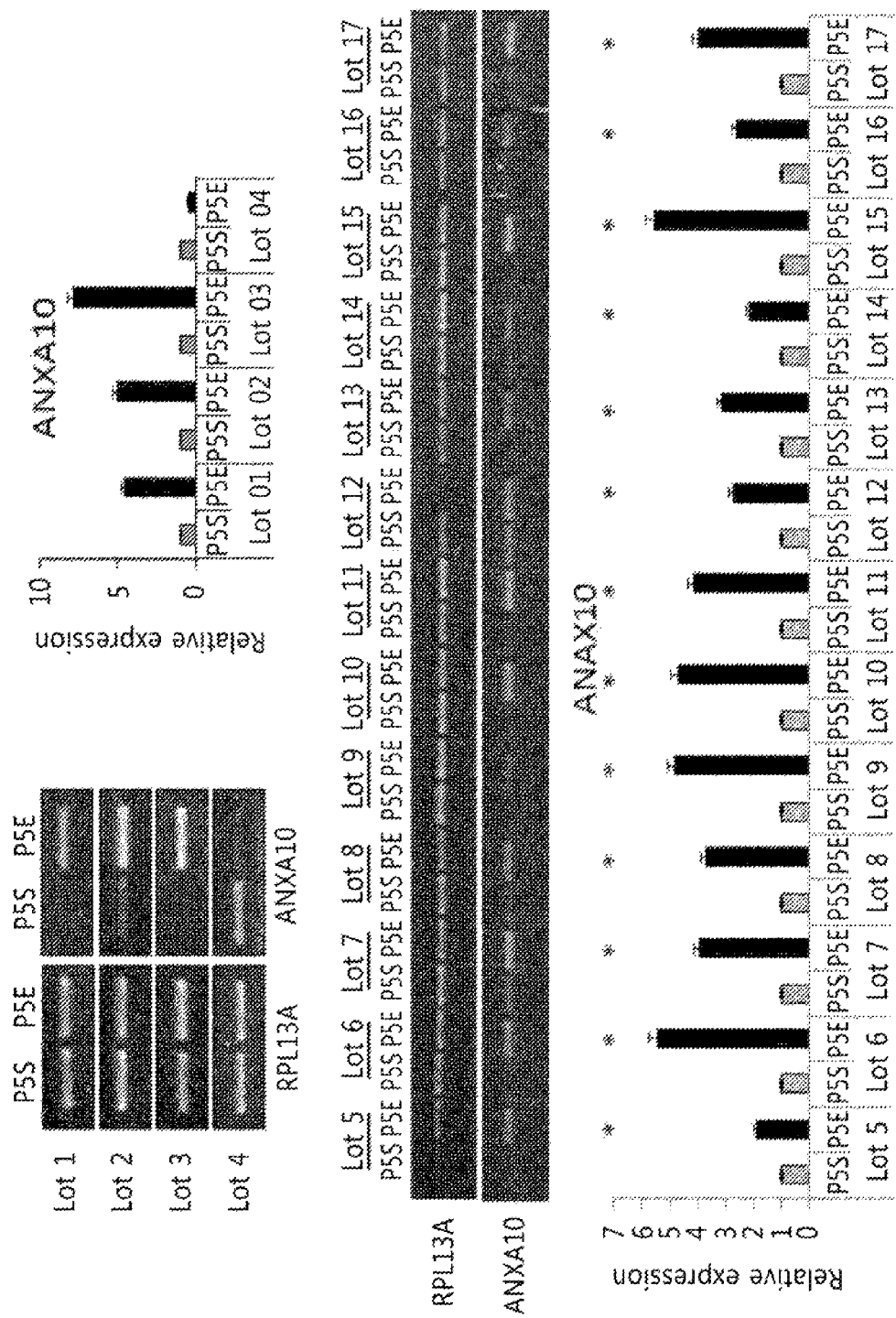
Figure 4C:
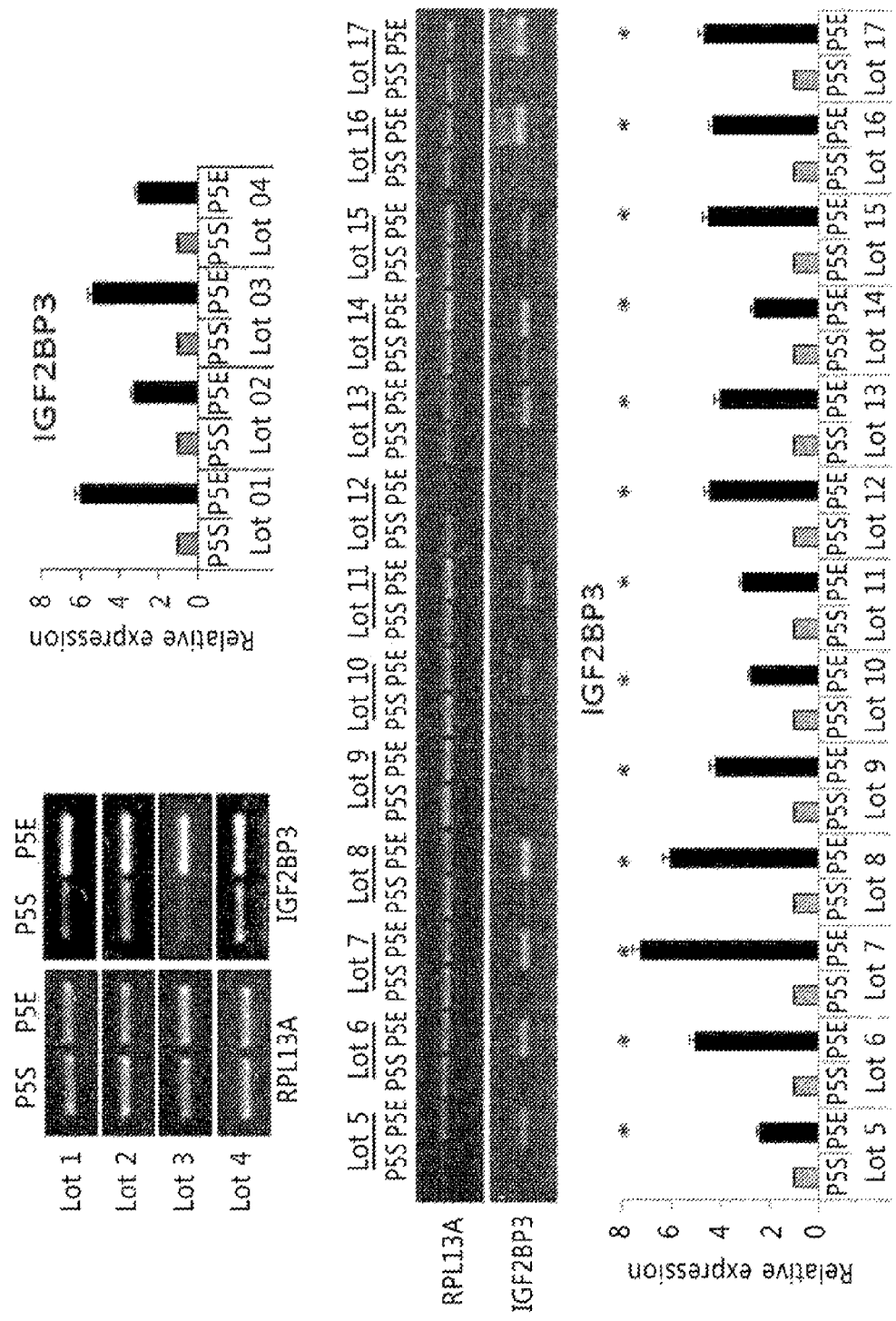
Figure 4D:
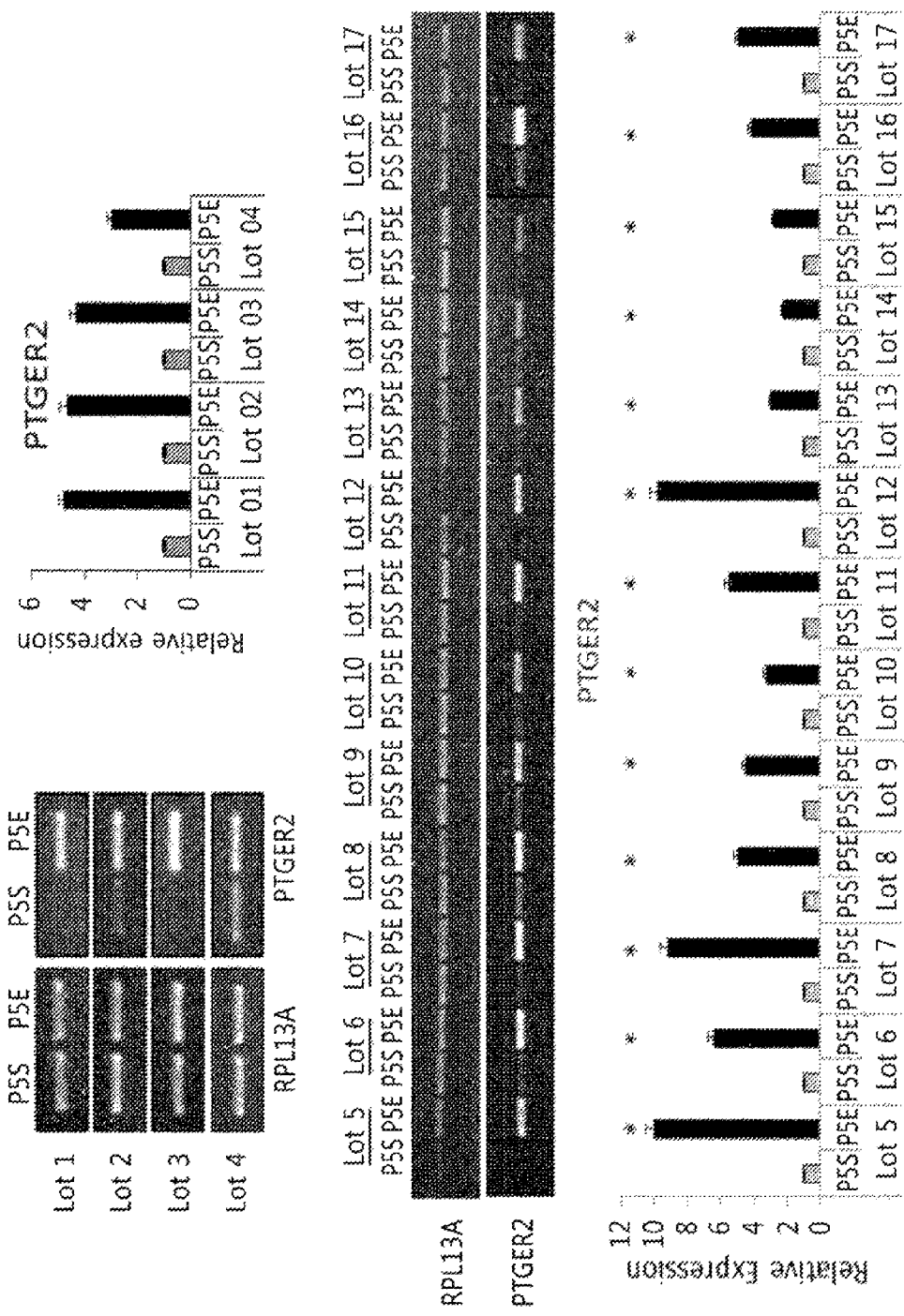

In an embodiment of the present invention, the expression differences between marker genes in adipose-derived stem cells cultured in a basal medium and a growth medium were confirmed via microarray (Example 2 and FIG. 3).

In another aspect, the present invention provides a kit for detecting a marker capable of detecting proliferation potential of adipose-derived stem cells cultured in a medium containing EGF or bFGF, comprising a composition for detecting a marker capable of detecting proliferation potential of the adipose-derived stem cells cultured in a medium containing EGF or bFGF.

The composition for detecting a marker capable of detecting proliferation potential of adipose-derived stem cells cultured in a medium containing EGF or bFGF, and the usable kit for detecting a maker are as described in the above.

In another aspect, the present invention provides a method for detecting differentiation potential of adipose-derived stem cells comprising a step of measuring the level of mRNA or a protein of at least one gene selected from the group consisting of AGPAT9, ANXA10, IGF2BP3, PTGER2, ITGA11, PAWR, and SFRP2 of adipose-derived stem cells cultured in a medium containing EGF or bFGF.

The medium containing EGF or bFGF, the measurement of mRNA or protein levels of the genes, and differentiation potential of adipose-derived stem cells are as described in the above.

The method may be a method for detecting differentiation potential of adipose-derived stem cells further comprising a step of determining that differentiation potential is higher than that of the control group when the amount of mRNA or protein of at least gene selected from the group consisting of ITGA11, PAWR, and SFRP2 is lower, or when the amount of mRNA or a protein of at least one gene selected from the group consisting of AGPAT9, ANXA10, IGF2BP3, and PTGER2 is higher than the amount measured in adipose-derived stem cells cultured in a basal medium, which is used as the control group.

Preferably, adipose-derived stem cells cultured in basal medium, which is the control group, and adipose-derived stem cells cultured in a growth medium are identical in generation or have a maximum of one generation difference.

In an embodiment of the present invention, based on that therapeutic activity such as proliferation potential, differentiation potential, etc., are superior in adipose-derived stem cells cultured in a medium containing EGF or bFGF compared to adipose-derived stem cells cultured in a basal medium not containing EGF or bFDF (KR Patent Application Publication No. 10-2010-0118491), genes which show a significant expression difference between adipose-derived stem cells cultured in a medium containing EGF or bFGF and adipose-derived stem cells cultured in a basal medium were examined, and results confirmed increased expressions of AGPAT9, ANXA10, IGF2BP3, and PTGER2, and reduced expressions of ITGA11, PAWR, and SFRP2 in adipose-derived stem cells cultured in a medium containing EGF or bFGF (FIGS. 4 and 5). Thus, adipose-derived stem cells with increased expressions of AGPAT9, ANXA10, IGF2BP3, and PTGER2, or reduced expression of ITGA11, PAWR, and SFRP2 exhibit superior differentiation potential compared adipose-derived stem cells with reduced expressions of fAGPAT9, ANXA10, IGF2BP3, and PTGER2, or increased expressions of ITGA11, PAWR, and SFRP2.

In another aspect, the present invention provides a method for detecting proliferation potential of adipose-derived stem cells comprising a step of measuring the level of mRNA or a protein of at least one gene selected from the group consisting of AGPAT9, ANXA10, IGF2BP3, PTGER2, ITGA11, PAWR, and SFRP2 of adipose-derived stem cells cultured in a medium containing EGF or bFGF.

The medium containing EGF or bFGF, measurement of mRNA or protein levels of the genes, and proliferation potential of adipose-derived stem cells are as described in the above.

Preferably, the method may be a method for detecting proliferation potential of adipose-derived stem cells further comprising determining that differentiation potential is higher than that of the control group when the amount of mRNA or a protein of at least one gene selected from the group consisting of ITGA11, PAWR, and SFRP2 is lower, or when the amount of mRNA or a protein of at least one gene selected from the group consisting of AGPAT9, ANXA10, IGF2BP3, and PTGER2 is higher than the amount measured in adipose-derived stem cells cultured in a basal medium, which is used as the control group.

MODE FOR INVENTION

Hereinafter, the present invention will be described more in detail with reference to Examples. However, Examples are for illustrative purposes only, and thus the scope of the present invention is not intended to be limited by the Examples.

Example 1: Examination of Cell Proliferation Potential of Adipose-Derived Stem Cells in a Basal Medium or a Growth Medium Example 1-1: Culturing Human Adipose-Derived Stromal Stem Cells Adipose tissues were separated from donors (Anterogen, Gyeonggi-do, Korea), and adipose-derived stem cells were isolated from the obtained adipose tissues. In order to remove blood, the adipose tissues were washed with the same volume of Krebs-Ringer Bicarbonate (KRB) solution for 34 times. The adipose tissues were added with the same volume of collagenase solution and allowed to react in a water bath at 37° C., transferred into a centrifuge tube, and centrifuged at 20° C. at a rate of 1200 rpm for 10 minutes. The adipose layer, which is the supernatant, was removed, and collagenase solution, which is the lower layer, was carefully separated, taking care not to shake. After suspending by adding a basal medium thereto, the separated layer was centrifuged at 20° C. at a rate of 1200 rpm for 5 minutes. Since the part that settles down on the bottom is a stromal vascular fraction, the supernatant was removed. The stromal vascular fraction was suspended in basal medium, inoculated onto a culturing container, and cultured in an incubator at 37° C. with 5% $CO_2$ for 24 hours. After removing the culture medium, the resultant was washed with a phosphate buffer solution, and proliferated in a basal medium, a basal medium containing bFGF at a concentration of 1 ng/mL, or basal medium containing EGF at a concentration of 5 ng/mL. When adipose-derived stem cells were proliferated to cover 80-90% of the culturing container, they were obtained as single cells by treating trypsin. The collected cells were diluted with a growth medium at a ratio of 1:31:4 and subcultured (KR Patent Application Publication No. 10-2010-0118491). In order to analyze expression differences according to the culture media compositions, the 5th generation cells cultured in a basal medium containing DMEM with 10% FBS, and the 5th generation cells cultured in a growth medium, which is a basal medium containing 1 ng/mL bFGF, were collected.

Culturing the total of 5 lots showed that the proliferation rate was faster and that the stable fibroblasts structure was maintained when cultured in a growth medium, compared to when cultured in a basal medium. FIG. 1 illustrates structures of adipose-derived stem cells cultured in a basal medium and a growth medium. FIG. 2 illustrates an example of cell population doubling level (CPDL) of adipose-derived stem cells cultured in a basal medium and a growth medium.

Example 2: Verification of Increased Gene Expressions Depending on Media Via Microarray Anal Example 2-1: Culturing Human Adipose-Derived Stem Cells Adipose tissues were separated from 17 donors (Anterogen, Gyeonggi-do, Korea), and adipose-derived stem cells were cultured in the same manner as in Example 1.

Example 2-2: Separating the Total RNA

The total RNA was isolated using QIAGEN kit (RNeasy Maxi kit: cat #75162), and quantified using Experion RNA StdSens chip (Bio-Rad). Firstly, the cultured adipose-derived stem cells were dissolved in 15 mL of a degradation buffer solution in the kit, to which 150 μL of beta mercaptoethanol is added. Thereto, 15 mL of 70% ethanol added and stirred, and centrifuged at 3000 g for 5 minutes, thereby adhering the total RNA to the membrane. After washing twice, RNA was isolated by adding 1.2 rat of RNase-free water.

Example 2-3: Performing a Microarray

The extracted total RNA was hybridized using illumina TotalPrep RNA Amplification Kit (Ambion). cDNA was synthesized using T7 Oligo (dT) primer, and biotin-labeled cRNA was prepared by in vitro transcription using biotin-UTP. The prepared cRNA was quantified using NanoDrop. cRNA prepared in adipose-derived stem cells was hybridized on Human-6 V2 chip (Illumina). After hybridization, the DNA chip was washed with Illumina Gene Expression System wash buffer (Illumina) in order to remove non-specific hybridization, and the washed DNA chip was labeled with streptavidin-Cy3 (Amersham) florescent staining agents. The florescent-labeled DNA chip was scanned with a confocal laser scanner (Illumina). Florescence data at each spot was obtained and saved as an image file in the TIFF format. TIFF image files were quantified using Bead-Studio version 3 (Illumina), thereby quantifying fluorescence at each spot. The quantified results were corrected using the 'quantile' option in Avadis Prophetic version 3.3 (Strand Genomics).

The results are shown in FIG. 3. FIG. 3 illustrates the expression differences between the $5^{th}$ generation cells cultured in a basal medium basal medium and in a growth medium. AGPAT9, ANXA10, IGF2BP3, and PTGER2 genes showed significantly increased expressions, and ITGA11, PAWR, and SFRP2 genes showed significantly reduced expressions in a growth medium, compared to a basal medium. The results suggest that the genes may be used to determine adipose-derived stem cells which were cultured in a clinically effective growth medium, as they showed remarkable expression differences between a basal medium and a growth medium. However, such results may be different from markers known to distinguish stem cells from differentiated to cells, and may also differ depending on the number of generations and differentiation. For example, IGF2BP3 expression increases in pre-differentiated stem cells following generations, but drastically decreases after differentiation is initiated. ITM2A expression decreases pre-differentiated stem cells following generations, but increases after differentiation is initiated.

Example 3: Individual Examination of Genes Which Show Expression Differences Between a Basal Medium and a Growth Medium in Adipose-Derived Stem Cells of Individual Donors Expression levels of genes confirmed in Example 2 were analyzed via RT-PCR using 17 pairs of adipose-derived stem cell samples from donors (cells cultured in a basal medium and a growth medium). The total RNA was isolated according to the method of Example 2.

Example 3-1: Synthesizing cDNA and Correcting Template Concentration

To each sample, 2 μg of the total RNA, 1 μL of 50 M Oligo (dT) primer, and 2.5 μL of 10 mM dNTP were added, and a total of 25 μL of RNA/primer mixed solution were prepared by adding sterile water containing DEPC, which is an RNase inhibitor. After reacting at 65° C. for 5 minutes, the mixed solution was stored at 55° C. Then, 5 μL of 10× RT buffer, 10 μL of 25 mM $MgCl_2$, 5 μL of 0.1 M DTI, 1 μL of RNase inhibitor, and 1 μL of SuperScriptIII PT enzyme were added to a final volume of 25 μL, and mixed with the RNA/primer mixed solution stored at 55° C., and the mixture was reacted at 55° for 50 minutes. Then, the mixture was reacted at 85° C. for 5 minutes to inactivate the RT enzyme, and the reaction was terminated by adding ice thereto. RPh13A was used as the control gene for quantifying marker genes. An RT-PCR reaction was performed using a primer for the control gene, and cDNA concentration was calibrated to equalize the expression level of the control gene RPL13A. A PCR reaction was performed using 2 μL of the sample after diluting each cDNA by 20 folds. The PCR reaction was performed using 15 μL of 2×PCR premix (Hot start), 2 μL it of forward primers for PRL13A, 2 μL of reverse primers for PRL13A, and 11 μL of distilled water, for 20 cycles, 23 cycles, and 25 cycles. Here, RT-PCR reaction conditions were 94° C. for 30 seconds, 50° C. for 30 seconds, and 72° C. for 1 minute. The forward primer used for RPL13A was 5'-CATCGTGGCTAAACAGG-TACTG-3' (SEQ ID NO: 1), and the reveres primer used was 5'-GCACGACCTTGAGGGCAGC-3' (SEQ ID NO: 2). PCR products were loaded on a 2% agarose gel, and gel images were photographed after electrophoresis. The concentration of each sample was equalized by quantifying the image using TotalLab v1.0 program (Nonlinear Dynamix), performing PCR after calibrations followed by quantification.

Example 3-2: Analyzing Expression Levels Using RT PCR/Real-Time PCR

PCR was performed using sense and antisense primers for cDNA, which was diluted to equalize the amounts. 3 μL of cDNA, 10 μL of 2× premix, 2 μL of each primer (20 pmole), and 2 μL of distilled water were added to a final volume of 20 μL of a solution. A PCR reaction was performed at 94° C. for 1 minute, at 54° C. for 30 seconds, and at 72° C. for 1 minute, and the number of PCR cycles performed was varied for each gene. In order to examine PCR products, electrophoresis was performed using a 2% agarose gel, and the results were analyzed using images tools. A real-time RT-PCR was performed using DNASYBRI reagents of Qiagen (CA, USA) and LightCycler (Roche). The quality of PCR products were examined via Melt Curve analysis, and gene expression were analyzed using LightCycler version 3.5 software (Roche). The primer sequences specific for genes used in the RT-PCR/Real-Time PCR and the reverse primers (SEQ ID NO: 1 to 16) are shown in Table 1.

The results are shown in FIGS. 4 and 5. It was demonstrated that the genes prominently increase or decrease in a growth medium compared to a basal medium. Therefore, AGPAT9 (94.1%, increased in 16 out of 17 samples), ANXA10 (94.1%, increase in 16 out of 17 samples), IGF2BP3 (100%, increased in 17 out of 17 samples), PTGER2 (100%, increased in 17 out of 17 samples) (FIG. 4 A-D), ITGA11 (94.1%, reduced in 16 out of 17 samples), PAWR (94.1%, reduced in 16 out of 17 samples), and SFRP2 (94.1%, reduced in 16 out of 17 samples) (FIG. 5 A-C) genes are marker capable of determining adipose-derived stem cells cultured in a growth medium, having increased clinical effects, and may be further used as a marker detecting precision of the quality of adipose-derived stem cells cultured using an improved culturing method.

TABLE 1

| Gene (REF) | Primer | SEQ ID NO |
|---|---|---|
| RPL13A(NM_012423.02) | F: 5'-catcgtggctaaacaggtact3' | SEQ ID NO: 1 |
|  | R: 5'-gcacgaccttgagggcagc-3' | SEQ ID NO: 2 |
| AGPAT9(NM_032717.3) | F: 5'-aatcttgacddcggatggat-3' | SEQ ID NO: 3 |
|  | R: 5'-caaaccagacatgaggacaa-3' | SEQ ID NO: 4 |
| ANXA10(NM_007193.3) | F: 5'-cgagacaaaccagcctattt-3' | SEQ ID NO: 5 |
|  | R: 5'-tggtcagcaggtctatttca-3' | SEQ ID NO: 6 |
| IGF2BP3(NM_006547.2) | F: 5'-cacctgatgagaatgaccaa-3' | SEQ ID NO: 7 |
|  | R: 5'-actttgcagagccttctgtt-3' | SEQ ID NO: 8 |
| PTGER2(NM_000956.2) | F: 5'-cacctcattctcctggctat-3' | SEQ ID NO: 9 |
|  | R: 5'-gaggtcccattttttcctttc-3' | SEQ ID NO: 10 |
| ITGA11(NM_001004439.1) | F: 5'-tgaggtccctaaaagcactc-3' | SEQ ID NO: 11 |
|  | R: 5'-cagtcctcttgcttggagat-3' | SEQ ID NO: 12 |
| PAWR(NM_002583.2) | F: 5'-caggagccacctagaacagt-3' | SEQ ID NO: 13 |
|  | R: 5'-tacctgaaacatttgcatcc-3' | SEQ ID NO: 14 |

TABLE 1-continued

| Gene (REF) | Primer | SEQ ID NO |
|---|---|---|
| SFRP2(NM_003013.2) | F: 5'-aaaatcatcctggagaccaa-3'<br>R: 5'-tgtcgttcatctcctcacag-3' | SEQ ID NO: 15<br>SEQ ID NO: 16 |

Example 4: Examining Protein Expressions of the Selected Genes Depending on Generations Using the adipose-derived stem cell samples from donors (cultured in a basal medium and a growth medium), expression levels of some of the genes identified in Example 3 were analyzed by quantifying proteins via Western blot analysis.

In particular, after washing the cells cultured on a 60 mm dish once with PBS, proteins of cells were prepared by adding a cold buffer solution for proteins (RIPA cell lysis buffer: 50 mM Tris-Cl (pH 7.5), 150 mM NaCl, 1% Nonidet P-40, 10% glycerol, 1 mM PMSF, 1 mM DTT, 20 mM NaF, 1 mM EDTA, and a protease inhibitor). After placing 30 μg of each prepared protein sample on a 10% or 12% sodium dodecyl sulfate polyacrylamide gel electrophoresis (SDS-PAGE) gel, the proteins were separated according to their size and immobilized onto PVDF membranes.

After dissecting the filter to which the proteins were immobilized into an appropriate size, antibodies corresponding to each protein were bound. Information on antibodies is as follows: anti-ANXA10 (Santa Cruz, sc-70009), anti-IGF2BP3 (Santa Cruz, sc-100766), anti-PTGER2 (abcam, ab16151), anti-ITGA11 (ab107858), anti-PAWR (Sigma A0545), and anti-ACTIN (Sigma, A5316). The amount of each protein was examined by bands using Immobilon™ Western blotting detection reagents (Millipore).

The results showed that ANXA10, IGF2BP3, and PTGER2 genes which were confirmed to have an increased mRNA level in a growth medium via RT-PCR among other genes, were observed to be compatible with mRNA experimental results, as the protein expression level was low in a basal medium and high in a growth medium. ITGA11 and PAWR genes whish have a decreased mRNA level in a growth medium following an increase in generation were also observed to be compatible with mRNA experimental results, as the protein expression level was high in a basal medium and low in a growth medium (FIG. 6).

Based on the above description, it should be understood by one of ordinary skill in the art that other specific embodiments may be employed in practicing the invention without departing from the technical idea or essential features of the present invention. In this regard, the above-described examples are for illustrative purposes only, and the invention is not intended to be limited by these examples. The scope of the present invention should be understood to include all of the modifications or modified form derived from the meaning and scope of the following claims or its equivalent concepts, rather than the above detailed description.

The invention claimed is:

1. A method for obtaining adipose-derived stem cells having increased therapeutic potential comprising:
    separately culturing adipose-derived stem cells in a basal medium and in such basal medium also containing EGF or bFGF;
    separately measuring for adipose-derived stem cells cultured in the basal medium and in the basal medium containing EGF or bFGF, the level of mRNA or of protein encoded by (A) the prostaglandin E receptor 2 (PTGER2) gene and (B) at least one gene selected from the group consisting of the genes encoding 1-acylglycerol-3-phosphate O-acyltransferase 9 (AGPAT9), annexin A10 (ANXA10), insulin-like growth factor 2 binding protein 3 (IGF2BP3), integrin alpha 11 (ITGA11), PRKC apoptosis WT1 regulator (PAWR), and secreted frizzled-related protein 2 (SFRP2); and
    recovering adipose-derived stem cells cultured in the basal medium containing EGF or bFGF, for which (A) the amount of mRNA or the protein encoded by the PTGER2 gene is higher than the amount of such mRNA or protein measured in adipose-derived stem cells cultured in the basal medium; and (B) either (1) the amount of mRNA or protein encoded by one of the AGPAT9, ANXA10, or IGF2BP3 gene is higher, or (2) the amount of mRNA or protein encoded by one of the ITGA11, PAWR, or SFRP2 gene is lower than the amount of such mRNA or protein measured in adipose-derived stem cells cultured in the basal medium, thereby obtaining adipose-derived stem cells having increased therapeutic potential.

2. The method according to claim 1, wherein the measurement of the mRNA level is performed by using a pair of primers or a probe which binds specifically to the gene.

3. The method according to claim 1, wherein the measurement of the protein level of the genes is performed by using an antibody specific to the protein.

4. A method for obtaining adipose-derived stem cells having increased proliferation potential comprising:
    separately culturing adipose-derived stem cells in a basal medium and in such basal medium also containing EGF or bFGF;
    separately measuring for adipose-derived stem cells cultured in the basal medium and in the basal medium containing EGF or bFGF, the level of mRNA or of protein encoded by (A) the prostaglandin E receptor 2 (PTGER2) gene and (B) at least one gene selected from the group consisting of the genes encoding 1-acylglycerol-3-phosphate O-acyltransferase 9 (AGPAT9), annexin A10 (ANXA10), insulin-like growth factor 2 binding protein 3 (IGF2BP3), integrin alpha 11 (ITGA11), PRKC apoptosis WT1 regulator (PAWR), and secreted frizzled-related protein 2 (SFRP2); and
    recovering adipose-derived stem cells cultured in the basal medium containing EGF or bFGF, for which (A) the amount of mRNA or the protein encoded by the PTGER2 gene is higher than the amount of such mRNA or protein measured in adipose-derived stem cells cultured in the basal medium; and (B) either (1) the amount of mRNA or the protein encoded by one of the AGPAT9, ANXA10, or IGF2BP3 gene is higher, or (2) the amount of mRNA or protein encoded by one of the ITGA11, PAWR, or SFRP2 gene is lower than the amount of such mRNA or protein measured in adipose-derived stem cells cultured in the basal medium, thereby obtaining adipose-derived stem cells having increased proliferation potential.

5. The method according to claim 4, wherein the measurement of the mRNA level of the genes is performed by using a pair of primers or a probe which binds specifically to the gene.

6. The method according to claim 4, wherein the measurement of the protein level of the genes is performed by using an antibody specific to the protein.

\* \* \* \* \*